(12) United States Patent
Paborji et al.

(10) Patent No.: US 9,744,157 B2
(45) Date of Patent: *Aug. 29, 2017

(54) COMBINATIONS OF SOLIFENACIN AND SALIVARY STIMULANTS FOR THE TREATMENT OF OVERACTIVE BLADDER

(71) Applicant: TheraVida, Inc., Mountain View, CA (US)

(72) Inventors: Mehdi Paborji, Cupertino, CA (US); Wendy Jade Limayo Hernandez, Redwood City, CA (US); Kenneth L. Duchin, Delray Beach, FL (US); Roger S. Flugel, Redwood City, CA (US)

(73) Assignee: TheraVida, Inc., San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/836,856

(22) Filed: Aug. 26, 2015

(65) Prior Publication Data

US 2016/0213650 A1    Jul. 28, 2016

Related U.S. Application Data

(63) Continuation of application No. 13/476,883, filed on May 21, 2012, now Pat. No. 9,132,124, which is a continuation of application No. 13/467,195, filed on May 9, 2012, now Pat. No. 8,940,763.

(60) Provisional application No. 61/484,658, filed on May 10, 2011.

(51) Int. Cl.
*A61K 31/4178* (2006.01)
*A61K 31/4725* (2006.01)

(52) U.S. Cl.
CPC ...... *A61K 31/4178* (2013.01); *A61K 31/4725* (2013.01)

(58) Field of Classification Search
CPC .................. A61K 31/4178; A61K 31/4725
See application file for complete search history.

(56) References Cited

U.S. PATENT DOCUMENTS

| | | | |
|---|---|---|---|
| 4,927,640 A | 5/1990 | Dahlinder et al. | |
| 6,149,943 A | 11/2000 | McTeigue et al. | |
| 6,419,954 B1 | 7/2002 | Chu et al. | |
| 6,482,837 B1 | 11/2002 | Wood | |
| 6,627,635 B2 | 9/2003 | Palermo | |
| 6,716,449 B2 | 4/2004 | Oshlack et al. | |
| 7,026,329 B2 | 4/2006 | Crain et al. | |
| 7,419,686 B2 | 9/2008 | Kaiko | |
| 7,666,894 B2 | 2/2010 | Paborji | |
| 7,678,821 B2 | 3/2010 | Paborji | |
| 7,781,472 B2 | 8/2010 | Paborji | |
| 8,470,864 B2 | 6/2013 | Paborji | |
| 8,940,763 B2 | 1/2015 | Paborji et al. | |
| 9,132,124 B2 | 9/2015 | Paborji et al. | |
| 2004/0185111 A1 | 9/2004 | Rubino et al. | |
| 2005/0287211 A1 | 12/2005 | Yoshida et al. | |
| 2007/0053995 A1 | 3/2007 | Paborji | |
| 2007/0077300 A1 | 4/2007 | Wynn et al. | |
| 2007/0224269 A1 | 9/2007 | Rubino et al. | |
| 2008/0207737 A1 | 8/2008 | Zinger et al. | |
| 2008/0254115 A1 | 10/2008 | Rubino | |
| 2008/0299393 A1 | 12/2008 | Wu et al. | |
| 2009/0017111 A1 | 1/2009 | Van Den Heuvel et al. | |
| 2009/0192228 A1 | 7/2009 | Wang | |
| 2009/0247628 A1 | 10/2009 | Gant et al. | |
| 2009/0275629 A1 | 11/2009 | Paborji | |
| 2009/0318522 A1 | 12/2009 | Paborji | |
| 2010/0137392 A1 | 6/2010 | Paborji | |
| 2010/0152263 A1 | 6/2010 | Paborji | |
| 2011/0244051 A1 | 10/2011 | Paborji et al. | |

(Continued)

FOREIGN PATENT DOCUMENTS

| CN | 101287462 | 10/2008 |
|---|---|---|
| EP | 1629834 | 3/2006 |

(Continued)

OTHER PUBLICATIONS

Hornberger, J. et al. "Recognition, diagnosis, and treatment of primary focal hyperhidrosis". J. Am. Acad. Dermatol. Aug. 2004, vol. 51, p. 274.
Kim, W.O. et al; "Treatment of generalized hyperhidrosis with oxybutynin in post-menopausal patients"; Acta Derm Venereal. 2010, vol. 90, p. 291.
Product and Technology website [on-line]. Theravida, Inc. Mar. 9, 2015 (Mar. 9, 2015) [web archive retrieved on Mar. 10, 2016]. Retrieved from the Internet URL: -http://web.archive.org/web/20 150309011535/htlp://theravida.com/product.html> and URL:http:// web .archive.org/web/20 150309011557 /http:/ / theravida .com/ technology .html>.
Aframian, D.J. et al., "Pilocarpine Treatment in a Mixed Cohort of Xerostomic Patients," Oral Diseases, (2007) 13:88-92.
Aromdee, Chantana et al., "A Pilot Study of the Disposition of Pilocarpine in Plasma, Saliva and Urine After a Single Oral Dose," European Journal of Pharmaceutical Sciences, (1999) 8:81-83.

(Continued)

*Primary Examiner* — Sarah Pihonak
(74) *Attorney, Agent, or Firm* — Michael B. Rubin; Khin K. Chin; Bozicevic, Field & Francis LLP (57) ABSTRACT

Disclosed herein are pharmaceutical compositions comprising a therapeutically effective amount of extended release solifenacin, or a pharmaceutically acceptable salt thereof, and a therapeutically effective amount of pilocarpine, or a pharmaceutically acceptable salt thereof. Also disclosed herein are methods of treating a patient suffering from overactive bladder, the method comprising identifying a patient in need thereof, and administering to the patient a therapeutically effective amount of extended release solifenacin, or a pharmaceutically acceptable salt thereof, and a therapeutically effective amount of pilocarpine, or a pharmaceutically acceptable salt thereof. Also disclosed herein are methods of alleviating a side effect of treatment for overactive bladder in a patient suffering therefrom, the method comprising identifying a patient in need thereof, and administering to the patient a therapeutically effective amount of extended release solifenacin, or a pharmaceutically acceptable salt thereof, and a therapeutically effective amount of pilocarpine, or a pharmaceutically acceptable salt thereof.

6 Claims, 2 Drawing Sheets

(56) References Cited

U.S. PATENT DOCUMENTS

| | | |
|---|---|---|
| 2011/0245294 A1 | 10/2011 | Paborji et al. |
| 2012/0201894 A1 | 8/2012 | Paborji et al. |
| 2012/0289543 A1 | 11/2012 | Paborji et al. |
| 2012/0289544 A1 | 11/2012 | Paborji et al. |
| 2014/0037713 A1 | 2/2014 | Wotton et al. |
| 2014/0105976 A1 | 4/2014 | Paborji et al. |

FOREIGN PATENT DOCUMENTS

| | | |
|---|---|---|
| JP | 2009507021 | 2/2009 |
| WO | WO 9405263 | 3/1994 |
| WO | WO 9709980 | 3/1997 |
| WO | 0119901 | 3/2001 |
| WO | WO 0134139 | 5/2001 |
| WO | WO 0154728 | 8/2001 |
| WO | 03013538 | 2/2003 |
| WO | WO 2004105735 | 12/2004 |
| WO | 2005046684 | 5/2005 |
| WO | WO 2005123042 | 12/2005 |
| WO | WO 2006132196 | 12/2006 |
| WO | WO 2007027675 | 3/2007 |
| WO | WO 2007029087 | 3/2007 |
| WO | WO 2007041367 | 4/2007 |
| WO | WO 2009019599 | 2/2009 |
| WO | 2009045796 | 4/2009 |
| WO | 2009057138 | 5/2009 |
| WO | WO 2009022354 | 10/2009 |
| WO | WO 2011123815 | 10/2011 |
| WO | WO 2011123836 | 10/2011 |
| WO | WO 2012154770 | 11/2012 |

OTHER PUBLICATIONS

Chancellor, Michael B. et al., "A Comparison of the Effects on Saliva Output of Oxybutynin Chloride and Tolterodine Tartrate," Clinical Therapeutics, (2001) 23:5: 753-760.

Chapple Christopher R., "Muscarinic Receptor Antagonists in the Treatment of Overactive Bladder," Urology, 55 (Supplement 5A), May 2000, 33-46.

Chapple, Christopher et al., "The Effects of Antimuscarinic Treatments in Overactive Bladder: A Systematic Review and Meta-Analysis," European Urology 48, (2005): 5-26.

Clemett, Delyth, et al; "Tolterodine a Review of its Use in the Treatment of Overactive Bladder"; Drugs & Aging; 18 (4): 277-304, (2001).

Detrol (R) Package Insert; Pfizer, Inc. Mar. 2008.

Diokno, Ananias et al., "Prospective, Randomized, Double-Blind Study of the Efficacy and Tolerability of the Extended-Release Formulations of Oxybutynin and Tolterodine for Overactive Bladder: Results of the OPERA Trial," Mayo Clin Proc. vol. 78, (2003): 687-695.

Eisai Inc., "Salagen: FDA Package Insert," Dec. 2009.

Facts & Comparisons (1984), p. 730.

Foote, Jenelle et al., "Treatment of Overactive Bladder in the Older Patient: Pooled Analysis of Three Phase III Studies of Darifenacin, an $M_3$ Selective Receptor Antagonist," European Urology 48, (2005): 471-477.

Gautam et al., "Cholinergic Stimulation of Salivary Secretion Studied with $M_1$ and $M_3$ Muscarinic Receptor Single- and Double-Knockout Mice"; Molecular Pharmacology, 66(2); 260-269 (Aug. 2004).

Harris, N.O. et al., "Infrared Spectral Characteristics of Pilocarpinestimulated Saliva of Normally Caries-resistant Animals Compared with Caries-resistant and—susceptible Humans," J. Dent. Res. 39, (1960), 810-811.

International Preliminary Report on Patentability issued Apr. 16, 2007 in PCT/US2006/033671.

Loscher, W. and Honack, D., "Withdrawal Precipitation by Benzodiazepine Receptor Antagonists in Dogs Chronically Treated with Diazepam or the Novel Anxiolytic and Anticonvulsant Beta-carboline Abecarnil," Naunyn Schmiedebergs Arch. Pharmacol. (1992), 345, 452-460.

MacDiarmid, Scott A. et al., "Efficacy and Safety of Extended Release Oxybutynin for the Treatment of Urge Incontinence: An Analysis of Data From 3 Flexible Dosing Studies," The Journal of Urology, vol. 174: (2005): 1301-1305.

Masters, Kim J., "Pilocarpine Treatement of Xerostmia Induced by Psychoactive Medications," American Journal of Psychiatry, 162(5): (2005):pp. 1023.

Nagao, Mitsuhiro, et al; "Effects of propiverine hydrochloride (propiverine) on the muscarinic receptor binding affinity in guinea pig tissues and on salivation in conscious dogs"; Folia Pharmacologica Japonica, vol. 113, No. 3; (1999); pp. 157-166.

Oki, Tomomi et al., "Demonstration of Bladder Selective Muscarinic Receptor Binding by Intravesical Oxybutynin to Treat Overactive Bladder," The Journal of Urology vol. 172: (2004): pp. 2059-2064.

Oki, Tomomi et al., "Comparitive Evaluation of Exocrine Muscarinic Receptor Binding Characteristics and Inhibition of Salivation of Solifenacin in Mice," Biol. Pharm. Bull, 29(7): (2006): 1397-1400.

Oki, Tomomi et al., "Muscarinic Receptor Binding, Plasma Concentration and Inhibition of Salivation After Oral Administration of a Novel Anti muscarinic Agent, Solifenacin Succinate in Mice," British Journal of Pharmacology, (2005) 145: 219-227.

Paborji, M. et al: "Phase I Evaluation of THVD-201. A Fixed-Dose Combination of Tolterodine and Pilocarpine, to Eliminate the Dry Mouth Side Effect of Anti-Muscarinic Therapy for Overactive Bladder" European Urology Supplements, vol. 10. No. 2; Mar. 22, 2011; p. 277. XP008152710.

Pattee, P.L., et al; Drug Treatment of the Irritable Bowel Syndrome: Drugs, vol. 44, No. 2; (1992); pp. 200-206.

Physicians' Desk Reference (PDR) (2002), pp. 229-2230.

Prescribing information for EMBEDA™, 2009.

Prescribing information for DETROL™, 2009.

Rappaport, Bob A., NDA Approval letter for EMBEDA™, Aug. 13, 2009.

Salah, R.S. et al., "Pilocarpine for Anticholinergic Adverse Effects Asscoaited with Desipramine Treatement"; American Journal of Psychiatry, 153(4): (1996): pp. 579.

SAJA Pharmaceuticals Co.: "Vesicare 10 mg and 5 mg" Sep. 26, 2007 (Sep. 26, 2007). p. 1. Retrieved from the internet: URL:http://www.sajaonline.net/pdf/Vesicare%201eaflet.pdf.

Serra, Denise B. et al., "QT and QTc Interval with Standard and Supratherapeutic Doses of Darifenacin, a Muscarinic $M_3$ Selective Receptor Antagonist for the Treatment of Overactive Bladder," Journal Clinical Pharmacology, (2005) 45: 1038-1047.

Siami, Paul et al., "A Multicenter, Prospective, Open-Label Study of Tolterodine Extended-Release 4 mg for Overactive Bladder: The Speed of Onset of Therapeutic Assessment Trial (STAT)", Clinical Therapeutics, 24 (4): (2002): 616-628.

Smulders, Ronald A. et al., "Pharmacokinetics and Safety of Solinfenacin Succinate in Healthy Young Men", Journal of Clinical Pharmacology, (2004) 44: 1023-1033.

St. Peter et al., "Pharmacokinetics of Pilocarpine in Subjects with Varying Degrees of Renal Function", J Clin Pharmacol, 40: 1470-1475, (2000).

Stedman's Medical Dictionary (published by Houghton Mifflin Company) (1995), p. 642.

Steers, William et al., "An Investigation of Dose Titration with Darifenacin, an $M_3$-Selective Receptor Antagonist", BJU International (2005) 95: 580-586.

Tiwari, Atul and Naruganahalli Krishna S., "Current and Emerging Investigational Medical Therapies for the Treatment of Overactive Bladder," Expert Opin. Investig. Drugs, (2006) 15(9): 1017-1037.

U.S. Department of Health and Human Services, Food and Drug Administration, Center for Drug Evaluation and Research (COER), "Guidance for Industry: Waiver of In Vivo Bioavailability and Bioequivalence Studies for Immediate-Release Solid Oral Dosage Forms Based on a Biopharmaceutics Classification System," Section II(C); Aug. 2000.

Versi, Eboo et al., "Dry Mouth with Conventional and Controlled-Releases Oxybutynin in Urinary Incontinence," Obstetrics & Gynecology, (2000) 95: 718-721.

(56) References Cited

OTHER PUBLICATIONS

Wall et al., "Pharmacotherapy of Xerostomia in Primary Sjogren's Syndrome"; Pharmacotherapy, 22(5), (2002), pp. 621-629.
Waldeck, Kristian et al., "Comparison of Oxybutynin and its Active Metabolite, N-Desethyl-Oxybutynin, in the Human Detrusor and Parotid Gland", The Journal of Urology vol. 157: (1997) 1093-109.
Watanabe, Kiyoshi, et al; "Oxybutynin hydrochloride: Effects of Oxybutynin hydrochloride on the Motilities of the Digestive Tracts and Urinary Bladder in Anesthetized Dogs"; Applied Pharmacology, vol. 31, No. 5; (1986); pp. 995-1106.
Yakushiji, T. et al., "Effects of Benzodiazepines and Non-Benzodiazepine Compounds on the GABA-induced Response in Frog Isolated Sensory Neurones", Br. J. Pharmacol. (1989), 98, 735-740.
Yoshida Akira et al: "The Forefront for Novel Therapeutic Agents Based on the Pathophysiology of Lower Urinary Tract Dysfunction: Bladder Selectivity Based on In Vivo Drug-Receptor Binding Characteristics of Antimuscarinic Agents for Treatment of Overactive Bladder"; Journal of Pharmacological Sciences, vol. 112. No. 2: (2010); pp. 142-150.
Zinner, Norman et al., "Trospium Chloride Improves Overactive Bladder Symptoms: A Multicenter Phase III Trial," Journal of Urology, (2004) 171: 2311-2315.
Olsson, et al. (2001) "Multiple dose pharmacokinetics of a new once daily extended release tolterodine formulation versus immediate release tolterodine"; Clin Pharmacokinet. 40(3):227-235.
"Pilocarpine". Drug Facts and Comparisons. 1996 Edition. pp. 2672-2675.

COMBINATIONS OF SOLIFENACIN AND SALIVARY STIMULANTS FOR THE TREATMENT OF OVERACTIVE BLADDER

RELATED APPLICATIONS

This application is a continuation of U.S. application Ser. No. 13/476,883 filed May 21, 2012, now U.S. Pat. No. 9,132,124, which is a continuation of U.S. application Ser. No. 13/467,195, filed May 9, 2012, now U.S. Pat. No. 8,940,763 by Mehdi Paborji et al., and entitled "COMBINATIONS OF SOLIFENACIN AND SALIVARY STIMULANTS FOR THE TREATMENT OF OVERACTIVE BLADDER," which in turn claims priority to U.S. Provisional Application No. 61/484,658, filed May 10, 2011, by Mehdi Parborji et al., and entitled "COMBINATIONS OF SOLIFENACIN AND SALIVARY STIMULANTS FOR THE TREATMENT OF OVERACTIVE BLADDER,", which is incorporated herein by reference in its entirety.

FIELD OF THE INVENTION

The present invention is in the field of pharmaceutical compositions and methods of using the same for the treatment of overactive bladder and reduction of various side effects thereof.

BACKGROUND OF THE INVENTION

Overactive bladder (OAB) is characterized by involuntary contractions of the detrusor muscle during bladder filling. These contractions may be asymptomatic or may cause the three common symptoms that clinically define OAB: frequency of urination; urgency; and urge, or reflex incontinence. Frequency is an increase in the number of micturitions, to as many as eight or more a day. Urgency is the strong and sudden desire to urinate. Urge incontinence, or reflex incontinence, is the situation where the urge to urinate cannot be controlled and the patient wets his/her clothing. Nocturia, or nighttime urinary frequency that disturbs sleep (more than twice a night), is often included as a fourth symptom. The symptoms of OAB may appear individually or together, and it is not known whether they have a pathologic or neurogenic cause.

Several classes of medications have been used to treat and manage OAB, including antimuscarinic agents. Antimuscarinic agents, which exert their effects at muscarinic receptors and suppress or diminish the intensity of involuntary detrusor muscle contractions, are the first-choice pharmacotherapy for OAB, and may be the only therapy available whose efficacy is not in question. Solifenacin succinate is an extensively studied antimuscarinic agent. A major limitation of the use of solifenacin is that it lacks specificity for bladder tissue, with resultant bothersome side effects, such as dry mouth, constipation, effects on cognition, impaired sleep, etc.

SUMMARY OF THE INVENTION

Disclosed herein are pharmaceutical compositions comprising a therapeutically effective amount of extended release solifenacin, or a pharmaceutically acceptable salt thereof, and a therapeutically effective amount of a muscarinic agonist. Also disclosed herein are methods of treating a patient suffering from overactive bladder, the method comprising identifying a patient in need thereof, and administering to the patient a therapeutically effective amount of extended release solifenacin (e.g. VESIcare®), or a pharmaceutically acceptable salt thereof, and a therapeutically effective amount of a muscarinic agonist. Also disclosed herein are methods of alleviating a side effect of treatment for overactive bladder in a patient suffering therefrom, the method comprising identifying a patient in need thereof, and administering to the patient a therapeutically effective amount of extended release solifenacin, or a pharmaceutically acceptable salt thereof, and a therapeutically effective amount of a muscarinic agonist.

DETAILED DESCRIPTION OF THE PREFERRED EMBODIMENTS

The major limitations of treatment of overactive bladder (OAB) are the dry mouth and constipation side effects. The current approach to address the dry mouth is development of sustained release of the active moiety, such as solifenacin in the form of VESIcare®, which is disclosed in U.S. Pat. No. 6,017,927, incorporated by reference herein in its entirety. However, patients taking the long-acting sustained release formulation of solifenacin still suffer from these side effects and thus their quality of life is hampered significantly to the extent that the majority of patients discontinue the mediations after about 4-6 months.

Thus, in the first aspect, the present invention relates to a pharmaceutical composition comprising a therapeutically effective amount of a sustained release formulation of solifenacin, or a pharmaceutically acceptable salt thereof, and a therapeutically effective amount of a muscarinic agonist.

Solifenacin, which has the chemical name (1S)-(3R)-1-azabicyclo[2.2.2]oct-3-yl 3,4-dihydro-1-phenyl-2(1H)-isoquinolinecarboxylate, is a muscarinic receptor antagonist. In some embodiments, solifenacin used in the compositions and methods disclosed herein is formulated similar to the product VESIcare® (as solifenacin succinate). In other embodiments, solifenacin is formulated as an orally disintegrating tablet, such as Vesicare® OD, marketed by Astellas.

Within the context of the present disclosure, a "muscarinic agonist" is a compound that modulates, i.e., agonizes, the activity of a muscarinic receptor either directly or indirectly. A muscarinic agonist acts directly on the muscarinic receptors when the muscarinic agonist itself binds to the muscarinic receptor and modulates its activity. A muscarinic agonist acts indirectly on the muscarinic receptors when the muscarinic agonist stimulates the production of an endogenous muscarinic agonist, which in turn agonizes the muscarinic receptors. An endogenous muscarinic agonist is a natural binding partner of the muscarinic receptors and is produced by the body of the subject itself. An example of an endogenous muscarinic agonist is acetylcholine.

In certain embodiments, the muscarinic agonists selected from the group consisting of pilocarpine, cevimeline, anethole trithione, aclatonium napadisilate, and yohimbine, or a pharmaceutically acceptable salt or prodrug thereof. In further embodiments, the muscarinic agonist is pilocarpine, or a pharmaceutically acceptable salt or prodrug thereof. In other embodiments, the second compound is cevimeline, or a pharmaceutically acceptable salt or prodrug thereof.

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, succinic acid, tartaric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl) methylamine, and salts thereof with amino acids such as arginine, lysine, and the like.

Throughout the present disclosure, when a particular compound is named, it is understood that the name refers to both the free base, or free acid, of the compound, and the pharmaceutically acceptable salts thereof. Thus, for example, the scope of the term "solifenacin" covers both the free base of solifenacin, i.e., (1S)-(3R)-1-azabicyclo[2.2.2]oct-3-yl 3,4-dihydro-1-phenyl-2(1H)-isoquinolinecarboxylate, and its various pharmaceutically acceptable salts, for example solifenacin succinate.

The compounds useful for the compositions and methods described herein may be used in various formulations. Certain formulations affect the rate at which the compound enters the blood stream of the patient. Thus, some formulations are immediate release formulations while other formulations are delayed release, sustained release, or extended release formulations.

Thus, in embodiments, disclosed herein are combinations where solifenacin, or a pharmaceutically acceptable salt thereof, is in an extended release formulation, while the muscarinic agonist is in an immediate release formulation. In other embodiments, both solifenacin, or a pharmaceutically acceptable salt thereof, and the muscarinic agonist are in an extended release formulation.

By "extended release formulation" of solifenacin it is meant a formulation of solifenacin, similar to that found in VESIcare®, where solifenacin is administered once a day.

The compositions described herein are particularly useful in alleviating the major side effects in the treatment of OAB, namely dry mouth, discomfort around the mouth, difficulty speaking secondary to dry mouth, degree of difficulty chewing food secondary to dry mouth, and/or lack of quality of sleep, improving tolerability, and enhancing patient compliance while increasing the patient's quality of life.

In another aspect, the present invention relates to a method of treating a patient comprising administering to a patient in need thereof a therapeutically effective amount of a sustained release formulation of solifenacin, or a pharmaceutically acceptable salt thereof, and a therapeutically effective amount of a muscarinic agonist.

A patient in need of the treatment methods disclosed herein may be a patient who suffers from overactive bladder. The patient may also be one who finds current therapies for overactive bladder uncomfortable and/or the side effects of the therapy, such as the dry mouth, intolerable enough so as to require adjunct therapy to alleviate the side effects. The patient may also be one who is considering discontinuing therapy for overactive bladder due to the side effects of the therapy. In some embodiments, a patient who is recently diagnosed with overactive bladder but yet has not been treated therefor is a patient in need of the treatment methods and compositions disclosed herein. In these embodiments, the patient begins the therapy using the methods and combinations disclosed herein so that the patient does not experience any of the side effects, or experience the side effects to a lesser degree.

In some embodiments solifenacin, or a pharmaceutically acceptable salt thereof, and the muscarinic agonist are administered more or less simultaneously. In other embodiments solifenacin, or a pharmaceutically acceptable salt thereof, is administered prior to the muscarinic agonist. In yet other embodiments, solifenacin, or a pharmaceutically acceptable salt thereof, is administered subsequent to the muscarinic agonist.

It should be noted that simply taking commercially available the muscarinic agonist, e.g., pilocarpine HCl, e.g., Salagen® tablets, or any other salivary gland stimulants in conjunction with an OAB drug is not effective to alleviate the dry mouth side effect. The disclosed methods of therapy and therapeutic combinations are directed to matching the pharmacokinetic profile of the muscarinic agonist with the pharmacokinetic profiles of solifenacin, or a pharmaceutically acceptable salt thereof.

The present inventors have surprisingly discovered that if the extended release formulation of solifenacin, or a pharmaceutically acceptable salt thereof, and the muscarinic agonist are administered such that the peak plasma concentration for solifenacin occurs at nearly the same time after administration as the peak plasma concentration for the muscarinic agonist, then the patient will not receive the most efficacious combination of the two compounds. That is, in this situation, the patient still suffers from dry mouth and the related side effects that would render the patient uncomfortable. Instead, if the two compounds are administered such that the peak plasma concentration for the muscarinic agonist occurs at a time before the peak plasma concentration for solifenacin, then the patient receives the maximum therapeutic effect of the combination.

Similarly, if the extended release formulation of solifenacin, or a pharmaceutically acceptable salt thereof, and the muscarinic agonist are administered such that the time point at which the lowest saliva flow occurs because of the action of solifenacin nearly corresponds to the time point at which the highest saliva flow occurs because of the action of the muscarinic agonist, then the patient will not receive the most efficacious combination of the two compounds. Instead, if the two compounds are administered such that the time point at which the lowest saliva flow occurs because of the action of solifenacin after the time point at which the highest saliva flow would have occurred because of the action of the muscarinic agonist in the absence of solifenacin, then the patient receives the maximum therapeutic effect of the combination.

In some embodiments in the above methods, solifenacin, or a pharmaceutically acceptable salt thereof, and the muscarinic agonist are administered such that the ratio of their plasma concentrations, at a given point in time following their administration, is a predetermined value. Those of ordinary skill in the art recognize that the ratio of plasma concentrations is not necessarily the same as the ratio of the amount of compound administered. Compounds are digested differently in the gut, pass the gut wall differently, and have a different rate of first-pass metabolism in the liver. Furthermore, the clearance rate by the kidney is different for various compounds. Thus, for example, even if two compounds are administered in equivalent molar amounts, their plasma concentrations at a point in time after the administration may be significantly different. The methods disclosed herein take into account the pharmacokinetics of drug intake and metabolism, such that the ratio of the two compounds at the time of administration is adjusted so that the two compounds would have a predetermined concentration ratio in the plasma.

Thus, the two compounds may be administered simultaneously, but be formulated such that the delay in their release causes maximum therapeutic effect for the patient. In some of the embodiments when the two compounds are administered simultaneously, the two compounds are within one dosage form.

In some embodiments the dosage form is designed as sustained release of one agent combined with either sustained release or immediate release of the second agent to ensure maximum therapeutic effect. Further the dosage from can be designed based on the pharmacokinetic profiles where the peak plasma concentration of one compound, for example the muscarinic agonist, corresponds to maximum amount of mouth dryness caused by solifenacin.

Thus, in another aspect, the present invention relates to a method of increasing intrinsic bladder capacity, comprising administering to a patient in need thereof a therapeutically effective amount of solifenacin, or a pharmaceutically acceptable salt thereof, and a therapeutically effective amount of a muscarinic agonist.

The term "pharmaceutical composition" refers to a mixture of a compound of the invention with other chemical components, such as diluents, lubricants, bulking agents, desentegrant or carriers. The pharmaceutical composition facilitates administration of the compound to an organism. Multiple techniques of administering a compound, for example oral, exist in the art. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

In certain embodiments, the same substance can act as a carrier, diluent, or excipient, or have any of the two roles, or have all three roles. Thus, a single additive to the pharmaceutical composition can have multiple functions.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen and desired pharmacokinetic profiles of each component of combination therapy. Any of the well-known techniques, carriers, and excipients may be used as suitable and as understood in the art; e.g., in Remington's Pharmaceutical Sciences, above.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipient with pharmaceutical combination of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

Many of the compounds used in the pharmaceutical combinations of the invention may be provided as salts with pharmaceutically compatible counterions. Pharmaceutically compatible salts may be formed with many acids, including but not limited to hydrochloric, sulfuric, acetic, lactic, tartaric, malic, succinic, and the like. Salts tend to be more soluble in aqueous or other protonic solvents than are the corresponding free acids or base forms.

Typically, the dose range of the composition administered to the patient can be from about 0.010 to 1000 mg/kg of the patient's body weight. The dosage may be a single one or a series of two or more given in the course of one or more days, as is needed by the patient. Note that for solifenacin and the muscarinic agonist, human dosages for treatment of at least some condition have been established. For example, for solifenacin the preferred dosage is between 0.1 mg to 50 mg, and the more preferred dosage is between 1 mg to 30 mg. Other dose ranges include between 1 to 20 mg, between 2 mg to 17 mg, between 5 to 15 mg, between 7 mg to 15 mg. The dose may also be at 1 mg, 2 mg, 3 mg, 4 mg, 5 mg, 6 mg, 7 mg, 8 mg, 10 mg, 12 mg, 14 mg, 16 mg, or 20 mg. For pilocarpine, the preferred dosage is between 0.1 mg to 50 mg, and the more preferred dosage is between 1 mg to 30 mg. Other dose ranges include between 2 to 20 mg, between 3 to 25 mg, and between 4 to 20 mg. The dose may also be at 1 mg, 2 mg, 3 mg, 4 mg, or 4.5 mg, 5 mg, 5.5 mg, 6 mg, 6.5 mg, 7 mg, 7.5 mg, 8 mg, 8.5 mg, 9 mg, 9.5 mg, 10 mg, 10.5 mg, 11 mg, 11.5 mg, 12 mg, 13 mg, 15 mg, and 20 mg.

Although the exact dosage can be determined on a drug-by-drug basis, in most cases, some generalizations regarding the dosage can be made. The daily dosage regimen for an adult human patient may be, for example, an oral dose of between 0.001 mg and 1000 mg of each ingredient, preferably between 0.01 mg and 500 mg, for example 1 to 200 mg or each ingredient of the pharmaceutical compositions of the present invention or a pharmaceutically acceptable salt thereof calculated as the free base or free acid, the composition being administered 1 to 4 times per day or per week. Alternatively the compositions of the invention may be administered by continuous delivery such as sustained, delayed, or extended release, preferably at a dose of each ingredient up to 500 mg per day. Thus, the total daily dosage by oral administration of each ingredient will typically be in the range 0.1 mg to 2000 mg. Suitably the compounds will be administered for a period of continuous therapy, for example for a day, a week or more, or for months or years.

The amount of composition administered will, of course, be dependent on the subject being treated, on the subject's weight, the severity of the affliction, the manner of administration and the judgment of the prescribing physician.

It will be understood by those of skill in the art that numerous and various modifications can be made without departing from the spirit of the present invention. Therefore, it should be clearly understood that the forms of the present invention are illustrative only and are not intended to limit the scope of the present invention.

EXAMPLES

The examples below are non-limiting and are merely representative of various aspects of the invention.

Example 1: Case Study for a Combination of Solifenacin and Pilocarpine

In this study, the effect of solifenacin (VESIcare®), pilocarpine, the combination of the two, and placebo was measured in separate, yet identical, studies in a single individual.
Study Protocol:
The following protocol was for a pilot human study to evaluate the extent of saliva flow rate following the administration of 10 mg VESIcare® capsule and 7.5 or 10 mg pilocarpine HCl tablet after about 1.5 or 2 hrs from solifenacin administration. The subject was a healthy, white, male, 53 years old. The subject performed the following:
1. Fast the night before.
2. No coffee or soda 8 hrs prior to taking the first dose.
3. Record time voiding and measure urine if possible.
4. Record extent of dryness of the mouth (Very dry, dry, and not dry).
5. Record any adverse event.
6. Chew a 1"×1" piece of Parafilm (American National Can (Neenah, Wis. 54956) Bar code No. 7-466676999) over 2 minutes.
7. Collect wetted Parafilm and saliva into a tared container (pre-weighed container).
8. Measure the amount of saliva collected.
9. Plot Saliva collected per 2 min time intervals against time.

The subject fasted overnight, but had 240 mL of water 1 hr prior to dose. The water continued ad lib until 1 hr pre and 1 hr post dose, other than 120 mL with VESIcare® and 120 mL with 2.5 mg or 5 mg Salagen tablet, or a combination thereof. For lunch, the subject consumed a light sandwich. No coffee, soda, or caffeinated or alcoholic beverages was consumed.

Figure 1:
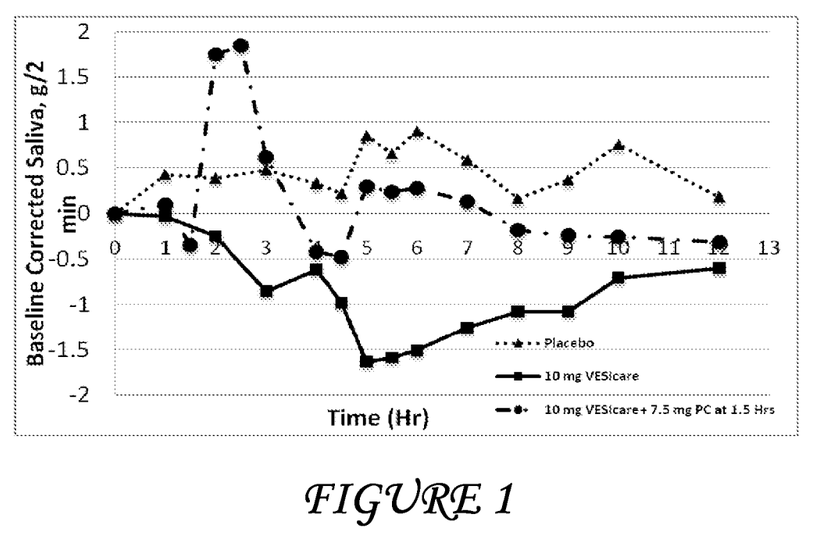
FIG. 1 is a graph showing the results of a clinical study on saliva formation when the subject was given a) no drug (▲); b) 10 mg VESIcare® (■); and c) 10 mg VESIcare® followed by 7.5 mg of pilocarpine 1.5 hours after the administration of solifenacin (●).

FIG. 1 shows three separate lines. The first (▲) is the baseline corrected saliva output for the subject during the course of 12 hours. The subject in this case did not take any medications, but followed the study protocol outlined above with respect to food and fluid intake. As the graph shows, there is a natural variation of less than about ±0.5 g/2 minutes of saliva during the course of the study. The second line (■) is the corrected saliva output for the subject having taken 10 mg VESIcare® during the course of 12 hours. The graph shows the extent of saliva output depression caused by solifenacin. The maximum dry mouth occurs at about 5 hours after the administration of solifenacin. The third line (●) shows the corrected saliva output for the subject having taken 10 mg VESIcare® followed by 7.5 mg of pilocarpine 1.5 hours after the administration of solifenacin. As can be seen, there is an increase in saliva output at the beginning, followed by slight saliva output depression.

Figure 2:
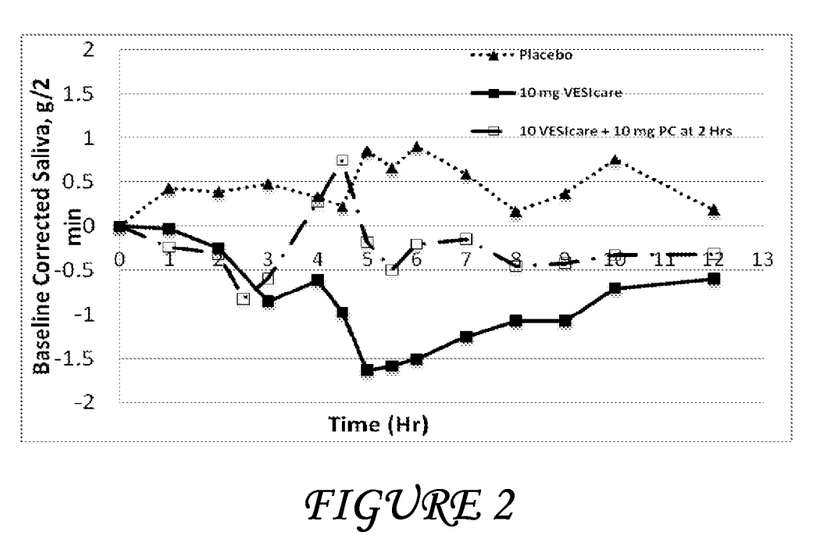
FIG. 2 is a graph showing the results of a clinical study on saliva formation when the subject was given a) no drug (▲); b) 10 mg VESIcare® (■); and c) 10 mg VESIcare® followed by 10 mg of pilocarpine 2 hours after the administration of solifenacin (□).

FIG. 2 shows three separate lines. The first two lines (▲ and ■) are identical to those of FIG. 1. The third line (□) shows the corrected saliva output for the subject having taken 10 mg VESIcare® followed by 10 mg of pilocarpine 2 hours after the administration of solifenacin. As can be seen, the maximum saliva output depression occurs around the same time as when no pilocarpine was administered, and the saliva output is depressed to a lesser extent as when no pilocarpine was administered.

Figure 3:
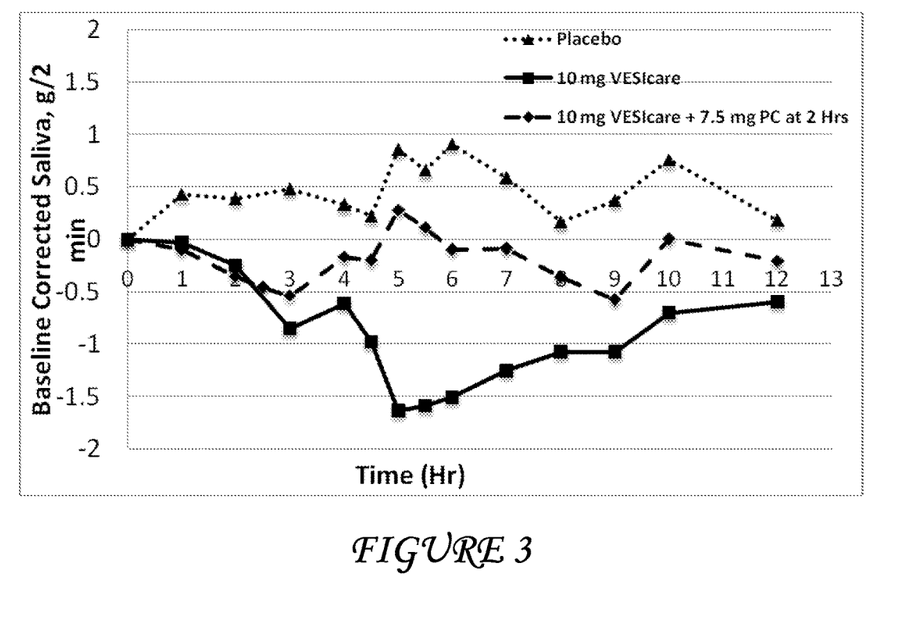
FIG. 3 is a graph showing the results of a clinical study on saliva formation when the subject was given a) no drug (▲); b) 10 mg VESIcare® (■); and c) 10 mg VESIcare® followed by 7.5 mg of pilocarpine 2 hours after the administration of solifenacin (♦).

FIG. 3 also shows three separate lines. The first two lines (▲ and ■) are identical to the respective lines of FIG. 1. The third line (♦) shows the corrected saliva output for the subject having taken 10 mg VESIcare® followed by 7.5 mg of pilocarpine 2 hours after the administration of solifenacin. As can be seen, the corrected saliva output for the third line hovers around the zero mark, indicating that this combination stabilizes the saliva generation.

The data in the FIGS. 1-3 are shown in tabular format below. Table 1 lists the absolute values of the weight of the collected saliva (g/2 min) at the various time points for the different study arms.

TABLE 1

| Time, Hrs | 10V[a] | 10V-7P-1[b] | 10V-7P-2[c] | 10V-10P-2[d] | Baseline |
|---|---|---|---|---|---|
| 0 | 3.01 | 2.96 | 2.99 | 3.07 | 2.64 |
| 1 | 2.98 | 3.06 | 2.89 | 2.84 | 3.07 |
| 1.5 | ND | 2.62 | ND | ND | ND |
| 2 | 2.76 | 4.72 | 2.635 | 2.76 | 3.04 |

TABLE 1-continued

| Time, Hrs | 10V[a] | 10V-7P-1[b] | 10V-7P-2[c] | 10V-10P-2[d] | Baseline |
|---|---|---|---|---|---|
| 2.5 | | 4.82 | 2.53 | 2.25 | ND |
| 3 | 2.155 | 3.58 | 2.449 | 2.48 | 3.12 |
| 4 | 2.395 | 2.54 | 2.82 | 3.35 | 2.98 |
| 4.5 | 2.03 | 2.49 | 2.79 | 3.82 | 2.87 |
| 5 | 1.375 | 3.26 | 3.267 | 2.89 | 3.5 |
| 5.5 | 1.42 | 3.2 | 3.1 | 2.58 | 3.3 |
| 6 | 1.5 | 3.24 | 2.89 | 2.87 | 3.55 |
| 7 | 1.755 | 3.09 | 2.9 | 2.93 | 3.23 |
| 8 | 1.935 | 2.78 | 2.627 | 2.62 | 2.81 |
| 9 | 1.935 | 2.72 | 2.415 | 2.66 | 3.02 |
| 10 | 2.305 | 2.71 | 2.99 | 2.74 | 3.40 |
| 12 | 2.41 | 2.65 | 2.78 | 2.76 | 2.83 |

[a]10V = 10 mg VESIcare ®
[b]10V-7P-1 = 10 mg VESIcare ® followed by 7.5 mg pilocarpine 1.5 hrs after VESIcare ®.
[c]10V-7P-2 = 10 mg VESIcare ® followed by 7.5 mg pilocarpine 2 hrs after VESIcare ®.
[d]10V-10P-2 = 10 mg VESIcare ® followed by 10 mg pilocarpine 2 hrs after VESIcare ®.
ND: Not determined.

Table 2 lists the baseline corrected values shown in Table 1. To obtain the values in Table 2, the value for time=0 hours in Table 1 is subtracted from the values for the other time points in each column.

TABLE 2

| Time, Hrs | 10V[a] | 10V-7P-1[b] | 10V-7P-2[c] | 10V-10P-2[d] | Baseline |
|---|---|---|---|---|---|
| 0 | 0 | 0 | 0 | 0 | 0 |
| 1 | −0.03 | 0.095 | −0.1 | −0.24 | 0.426 |
| 1.5 | ND | −0.345 | ND | ND | ND |
| 2 | −0.25 | 1.75 | −0.355 | −0.315 | 0.39 |
| 2.5 | ND | 1.85 | −0.46 | −0.825 | ND |
| 3 | −0.855 | 0.616 | −0.541 | −0.595 | 0.48 |
| 4 | −0.615 | −0.42 | −0.17 | 0.275 | 0.33 |
| 4.5 | −0.98 | −0.479 | −0.2 | 0.75 | 0.222 |
| 5 | −1.635 | 0.295 | 0.277 | −0.185 | 0.855 |
| 5.5 | −1.59 | 0.235 | 0.11 | −0.496 | 0.655 |
| 6 | −1.51 | 0.28 | −0.1 | −0.206 | 0.905 |
| 7 | −1.255 | 0.13 | −0.09 | −0.145 | 0.585 |
| 8 | −1.075 | −0.185 | −0.363 | −0.455 | 0.164 |
| 9 | −1.075 | −0.245 | −0.575 | −0.418 | 0.37 |
| 10 | −0.705 | −0.255 | 0 | −0.331 | 0.754 |
| 12 | −0.6 | −0.3126 | −0.21 | −0.318 | 0.184 |

As can be seen from the data, the maximum saliva depression point for VESIcare® occurs at about 6 hours after its administration. Previous studies, for example FIG. 1 of U.S. Pat. No. 7,678,821, which figure and the related discussion in the specification are incorporated by reference herein, have shown that maximum saliva output due to 5 mg of pilocarpine occurs about 30 minutes after its administration. One would expect for pilocarpine to retard the saliva depression of VESIcare® most effectively, pilocarpine would need to be administered about 30 minutes before the maximum depression point due to VESIcare®. That is, one would expect that pilocarpine would need to be administered about 5.5 hours after the administration of VESIcare®. However, the results presented herein show unexpectedly that best results are obtained when pilocarpine is administered at about 2 hours after the administration of VESIcare®.

Example 2: Clinical Study Protocol Synopsis

A study was conducted to evaluate the effect of solifenacin (VESIcare®) and pilocarpine in overactive bladder patients. The objectives of the study were to determine degree of dry mouth after oral administration of solifenacin and pilocarpine, and to determine the effect of the combination on number of voids, and number of incontinence episodes.

Subjects who have reasonable control of OAB symptoms (urinary frequency ≤13 voids/day and ≤1 incontinence episode/day) and have good tolerability (excluding dry mouth) while taking a stable dose of VESIcare® (10 mg/day) were recruited to participate in this evaluation. All subjects were administered VESIcare® for at least 4 to 6 weeks before being administered the combination therapy. The subjects were asked to record their OAB symptoms and status of dry mouth symptoms in a 3-day diary.

The subjects were asked to take pilocarpine (7.5 mg) at 2 hours after VESIcare® is taken. The combination was given for at least 2 weeks (Period 1) and then continued for another two weeks (Period 2). At the end of each 2-week period, a 3-day diary for voiding function, incontinence episodes, and dry mouth evaluation was collected.

Data related to voiding information were collected in diaries that were recorded over 3 consecutive days at the end of each treatment period. Self-assessments of dry mouth and other related activities/functions were made using validated 100 mm visual analog scales (VAS) that were completed on each of the three diary days. On the VAS, the value of 0 mm meant that there was no adverse symptom, whereas the value of 100 mm meant that the adverse symptom was at a highly intolerable level. The average value obtained over the 3 days was used as the value for the treatment period whether it was baseline (VESIcare® alone) or the study periods (combination of VESIcare® and pilocarpine).

The mean value (±standard deviation (SD)) for each 3-day measurement for each patient was calculated. The data point before the commencement of Period 1 was considered to be baseline. Baseline correction was applied by subtracting the baseline value from the data point at the end of Periods 1 and 2. The baseline corrected values are shown in the tables below.

Table 3 shows the baseline corrected value for the number of voids (micturitions) per day and the number of incontinence episodes (IE) per day. As can be seen, the addition of pilocarpine to VESIcare® does not adversely affect the efficacy of VESIcare®, because the number of micturitions and IEs do not worsen after the introduction of pilocarpine. Therefore, the addition of a muscarinic agonist to the muscarinic antagonist therapy does not alter the mechanism of action of the antagonist.

TABLE 3

Variation of Change from Baseline in Micturition and Incontinence Episodes of Solifenacin (VESIcare) with Treatment

| Subject No. | Change from Baseline in Micturition Per Day* | | | Change from Baseline in Incontinence Episodes | |
|---|---|---|---|---|---|
| | Baseline | Period 1 | Period 2 | Period 1 | Period 2 |
| 001 | 0.0 | 0.7 | 1.7 | −0.3 | −0.3 |
| 002 | 0.0 | −2.0 | −1.3 | −0.7 | −0.7 |
| 003 | 0.0 | −0.7 | 0.0 | −0.7 | −0.7 |
| 004 | 0.0 | −1.0 | −0.3 | 0.0 | 0.0 |
| 005 | 0.0 | −2.0 | −2.0 | 0.0 | 0.0 |
| Mean | 0.0 | −1.0 | −0.4 | −0.3 | −0.3 |
| SD | 0.0 | 1.1 | 1.4 | 0.3 | 0.3 |

*Each value represents mean of micturition value per day collected over a 3-consecutive day period.

More significantly, the dry mouth and the related adverse symptoms decrease significantly. Table 4 shows the baseline corrected VAS values for dry mouth. As can be seen, at the end of both Period 1 and Period 2 the VAS value decreases significantly. The data clearly show that pilocarpine can effectively negate the adverse dry mouth effect of VESIcare® in this study. It is significant to note that the change from baseline VAS did not change from Period 1 to Period 2, showing that the effect of the addition of pilocarpine to VESIcare®-therapy is consistent throughout the study.

TABLE 4

Variation of Change from Baseline in VAS Values of Dry Mouth of Treatment with Solifenacin (VESIcare)

| Subject No. | Baseline | Change from Baseline in VAS* | |
|---|---|---|---|
| | | Period 1 | Period 2 |
| 001 | 0.0 | −21.7 | −18.7 |
| 002 | 0.0 | −26.7 | −47.0 |
| 003 | 0.0 | −16.3 | −33.7 |
| 004 | 0.0 | −30.0 | −55.0 |
| 005 | 0.0 | −36.3 | −36.7 |
| Mean | 0.0 | −26.2 | −38.2 |
| SD | 0.0 | 7.7 | 13.8 |

*Each value represents mean of VAS scores of dry mouth collected over a 3-consecutive day period.

Table 5 shows the VAS values for other, secondary adverse symptoms related to dry mouth. These include the general feeling in the mouth, quality of sleep, ease of speaking, and ease of swallowing. As the data show, all of these metrics also improved in a sustained and consistent way when pilocarpine was added to VESIcare®-therapy.

TABLE 5

Variation of Change from Baseline in VAS Values of other Dry Mouth Related Adverse Symptoms of Treatment with Solifenacin (VESIcare)

| Subject No. | Baseline | Feeling in Mouth | | Sleeping | | Speaking | | Swallowing | |
|---|---|---|---|---|---|---|---|---|---|
| | | Period 1 | Period 2 | Period 1 | Period 2 | Period 1 | Period 2 | Period 1 | Period 2 |
| 001 | 0.0 | −24.3 | −25.0 | −0.3 | −3.7 | −3.3 | −5.0 | −12.7 | −14.3 |
| 002 | 0.0 | −24.0 | −37.3 | −53.7 | −65.0 | −33.0 | −37.7 | −12.0 | −12.0 |
| 003 | 0.0 | −20.0 | −37.7 | −27.0 | −35.0 | −37.0 | −52.0 | −11.7 | −28.3 |
| 004 | 0.0 | −15.3 | −53.3 | −2.3 | −32.0 | −14.7 | −56.0 | −5.0 | −16.7 |
| 005 | 0.0 | −36.7 | −37.0 | −35.0 | −34.0 | −36.0 | −34.7 | −34.7 | −34.0 |
| Mean | 0.0 | −24.1 | −38.1 | −23.7 | −33.9 | −24.8 | −37.1 | −15.2 | −21.1 |
| SD | 0.0 | 7.9 | 10.1 | 22.6 | 21.7 | 15.0 | 20.1 | 11.3 | 9.6 |

*Each value represents mean of VAS scores collected over a 3-consecutive day period Example 3: Clinical Study Protocol Synopsis A study is conducted to evaluate the effect of single doses of solifenacin (VESIcare®) and pilocarpine, alone and in combination versus placebo on salivary output in healthy volunteers. The objectives of the study are to determine salivary flow and degree of dry mouth after oral administration of solifenacin and pilocarpine, alone and in combination, vs. placebo, and to determine the effect of solifenacin and pilocarpine, alone and in combination, on urine volume/void and vital signs.

At each treatment period, following an overnight fast, subjects enter the clinic and after baseline measurements have been made, they are randomized to one of the following groups:

Solifenacin (VESIcare®, 10 mg) followed 2 hours later by placebo
Pilocarpine (5 mg) followed 2 hours later by placebo
Placebo followed 2 hours later by placebo
Solifenacin (VESIcare®, 10 mg) followed 2 hours by pilocarpine (7.5 mg)
Solifenacin (VESIcare®, 10 mg) followed 4 hours by pilocarpine (7.5 mg)

The following measurements are made just prior to and at frequent intervals for up to 12 hours post dose:
Salivary flow is determined by chewing a piece of Parafilm for 2 minutes
Degree of dry mouth is determined by visual analog scale (VAS)
Urine volume/void and frequency over 12 hours post dose is measured
Blood samples are taken for pharmacokinetics at pre-dose, and at, 1, 2, 4, 6, 10, 12 and 24 hours post dose
Food and water intake are standardized over the first 12 hour period The study is a double blind, randomized, placebo-controlled, with sequences (5 treatments over 5 weeks) with the drugs being administered orally as a single dose. There is a one-week washout between treatments. The study population is chosen as follows:
Healthy volunteers
12 subjects
≥18 years males or non-pregnant females
Weight 18-28 kg/m² BMI
No known allergy to antimuscarinic agents
No previous history of glaucoma, urinary retention, cardiac arrhythmias
No OTC medications, nutriceuticals or vitamins within 10 days of study enrollment and throughout the study Assessments (except for urine output) is performed at: 0.5 hr and within 10 minutes pre-dose, 1, 2, 4, 8, 12, and 24 hours post dose. The following are assessed:
1) Stimulated salivary flow
2) Degree of dry mouth (VAS)
3) Urine volume/void over 12 hours post dose
4) Pharmacokinetics of solifenacin and pilocarpine The standard safety precautions, such as physical exam, medical history, con-meds, ECG, hematology, clinical chemistry, urinalysis performed at screening and study termination, urine drug/alcohol screening at pre-dose for each period, vital signs (HR and BP) at: pre-dose, and at 2 hour intervals for 12 hours, and an awareness of adverse events throughout and between study period, are taken.

What is claimed is:
1. A method of alleviating dry mouth resulting from treatment with solifenacin in a patient, the method comprising:

administering orally to a patient a therapeutically effective amount of solifenacin or a pharmaceutically acceptable salt thereof; and administering orally a muscarinic agonist to the patient to alleviate the dry mouth, wherein the muscarinic agonist is administered about 2 hours after the solifenacin is administered and wherein the solifenacin is a once-a-day solifenacin composition.

2. The method according to claim 1, wherein the dry mouth further comprises discomfort around the mouth, difficulty speaking secondary to dry mouth and difficulty chewing food secondary to dry mouth.

3. The method according to claim 1, wherein the solifenacin or pharmaceutically acceptable salt thereof is administered in a dose of from 0.1 mg to 50 mg.

4. The method according to claim 1, wherein the solifenacin or pharmaceutically acceptable salt thereof is administered in a dose selected from the group consisting of 1 mg, 2 mg, 3 mg, 4 mg, 5 mg, 6 mg, 7 mg, 8 mg, 10 mg, 12 mg, 14 mg, 15 mg, 16 mg and 20 mg.

5. The method according to claim 1, wherein the muscarinic agonist is administered in a dose of from 0.1 mg to 50 mg.

6. The method according to claim 1, wherein the muscarinic agonist is administered in a dose selected from the group consisting of 1 mg, 2 mg, 3 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 10.5 mg, 11 mg, 11.5 mg, 12 mg, 13 mg and 15 mg.

\* \* \* \* \*